United States Patent
Pfleger (10) Patent No.: US 6,997,556 B2
(45) Date of Patent: Feb. 14, 2006

(54) METHOD FOR DETECTING, EVALUATING, AND ANALYZING LOOK SEQUENCES

(76) Inventor: Ernst Pfleger, Reichsapfelgasse 20/4, 1150 Vienna (AT)

( * ) Notice: Subject to any disclaimer, the term of this patent is extended or adjusted under 35 U.S.C. 154(b) by 0 days.

(21) Appl. No.: 10/262,608

(22) Filed: Sep. 30, 2002

(65) Prior Publication Data

US 2003/0086061 A1 May 8, 2003

Related U.S. Application Data

(60) Provisional application No. 60/326,257, filed on Oct. 1, 2001.

(30) Foreign Application Priority Data

Oct. 1, 2001 (AT) .............................. A 1551/2001

(51) Int. Cl.
*A61B 3/00* (2006.01)
*A61B 3/14* (2006.01)
*G06K 9/00* (2006.01)
*G01C 17/00* (2006.01)
*G06F 15/00* (2006.01)

(52) U.S. Cl. ...................... 351/246; 351/209; 382/103; 702/150; 702/187

(58) Field of Classification Search ................ 351/209, 351/210, 237; 345/7–9; 382/103, 107, 100, 382/106; 600/558; 702/150

See application file for complete search history.

(56) References Cited

U.S. PATENT DOCUMENTS

| | | | | |
|---|---|---|---|---|
| 5,231,674 A | * | 7/1993 | Cleveland et al. | 351/210 |
| 5,583,795 A | * | 12/1996 | Smyth | 702/150 |
| 5,886,683 A | * | 3/1999 | Tognazzini et al. | 715/700 |
| 6,090,051 A | * | 7/2000 | Marshall | 351/210 |
| 6,106,119 A | * | 8/2000 | Edwards | 351/209 |
| 6,120,461 A | * | 9/2000 | Smyth | 351/209 |
| 6,373,961 B1 | * | 4/2002 | Richardson et al. | 382/103 |
| 6,381,339 B1 | * | 4/2002 | Brown et al. | 382/103 |
| 6,601,021 B1 | * | 7/2003 | Card et al. | 702/187 |

* cited by examiner

*Primary Examiner*—Eleni Mantis-Mercader
*Assistant Examiner*—John R. Sanders
(74) *Attorney, Agent, or Firm*—Henry M. Feiereisen (57) ABSTRACT

In a method for detecting, evaluating, and analyzing look sequences of a test person using a look detection system, the field of view of the test person is detected by a first camera, which is directed forwardly and firmly held on the person's head, and recorded in a field of view video. The movement of the pupils is detected by a second camera, also firmly held on the person's head and recorded in an eye video. The pupil coordinates for each frame of the eye video are determined by automatically measuring the contrast of the pupils relative to the surrounding areas with an image recognition program, and the centroid of the dark area, which corresponds to the pupil center having the pupil coordinates is established. A correlation function between pupil coordinates in the eye video and the coordinates of the corresponding visual point is determined in the field of view video. Subsequently, the coordinates of the corresponding visual point in the field of view video are extrapolated from the pupil coordinates for each frame in the eye video.

18 Claims, 6 Drawing Sheets

METHOD FOR DETECTING, EVALUATING, AND ANALYZING LOOK SEQUENCES

CROSS-REFERENCES TO RELATED APPLICATIONS

This application claims the benefit of prior filed provisional application, Appl. No. 60/326,257, filed Oct. 1, 2001, pursuant to 35 U.S.C. 119(e), the disclosure of which is incorporated herein by reference.

This application claims the priority of Austrian Patent Application, Serial No. A1551/2001, filed Oct. 1, 2001, pursuant to 35 U.S.C. 119(a)–(d), the disclosure of which is incorporated herein by reference.

BACKGROUND OF THE INVENTION

The present invention relates to a method for detecting, evaluating, and analyzing look sequences of a test person, and more particularly to a method for detecting the pupil coordinates of the eye in relation to a target with a look detection system.

Methods for detecting, evaluating, and analyzing look sequences are known in the art, whereby the field of view of a test person is detected by a first camera, which points forward and is rigidly held on the head of the test person. The first camera image is recorded in a field of view video. The pupil movement of the test person is detected with a second camera, which is also rigidly held on the head of the test person. This second camera image is recorded as an eye video. The eye video and the field of view video are recorded by a video system and synchronized in time, whereby the pupil coordinates are determined for each frame of the eye video. A correlation function is determined on the field of view video between pupil coordinates on the eye video and the coordinates of the corresponding visual point, i.e., the point upon which the test person fixes. After the correlation function has been determined, the coordinates of the corresponding visual point on the field of view video are extrapolated for each frame from the pupil coordinates on the eye video.

However, with these methods, the pupil coordinates are detected either not at all or very imprecisely and in a very expensive way.

It would therefore be desirable and advantageous to provide an improved method which reliably recognizes the pupil coordinates for each frame of the eye video with minimum technical complexity.

SUMMARY OF THE INVENTION

According to one aspect of the invention, the pupil coordinates for each frame of the eye video are automatically established by using an image recognition program, which registers the contrast of the pupils to the surrounding area, searches for all points of the frame which are darker than a preset degree of darkness, and with the help of these points, detects and delimits completely a dark area corresponding to the pupils, and determines the centroid of the dark area, which corresponds to the pupil center having the pupil coordinates.

With this method, first the entire pupil is detected as a dark area. The registration of the contrast between the dark pupil and the nearly white surroundings of the pupils allows particularly simple automatic detection of the dark area. Establishing the centroid of this dark area is performed in a particular simple way without requiring substantial computer resources, the centroid able to be indicated with great precision, however. By equating the pupil center to the centroid of the dark area, the pupil center may be established with great precision in a particularly simple way. The present invention is based on the general principle known in the related art of combining an eye video and a field of view video, and, due to the newly developed optical and mathematical methods in the background and the new analysis methods resulting therefrom, represents a significant innovation.

In order to correct errors due to unforeseen interference or incidences of light, according to a further embodiment of the present invention, the pupil coordinates are corrected by hand after the automatic establishment of the pupil coordinates.

A further problem in methods for detecting, evaluating, and, analyzing look'sequences of the type initially described is the imprecision in establishing the correlation function.

It is therefore also desirable to improve the known systems and provide a method in which reliable establishment of the correlation function may be performed with the lowest possible technical outlay.

This is achieved according to the present invention in that, to establish the correlation function, first, one or more sample look sequences of the test person on one or more specific, predetermined control points are recorded and the assignment of the pupil coordinates on the eye video to the coordinates of the control points on the, field of view video is established, in that the pupil coordinates in the eye video are established for each frame in the eye video, the coordinates of the control points in the corresponding frame on the field of view video are established, the pupil coordinates in the frame of the eye video are assigned to the coordinates of the control point in the corresponding frame of the field of view video, this data set is stored, and the pupil coordinates on the eye video and the coordinates of the corresponding visual point on the field of view video are correlated from all data sets, preferably through quadratic regression.

With this method, a correlation function is obtained which is based on corresponding coordinates on each frame of the eye video and of the field of view video. Therefore, an unusually high precision of the correlation function results, the establishment thereof able to be performed in a simple way.

In order to determine the correlation function largely automatically, in a further implementation of the present invention, the coordinates of the control point on each frame of the field of view video are automatically established through an image recognition method.

According to another variant of the present invention, the coordinates of the control point on each frame of the field of view video may be established by hand with a mouse click. In this way, these coordinates may be established reliably even in the event of difficult conditions, such as insufficient contrast or undesired reflected glare due to flashes, etc.

In a further embodiment of the present invention, the sample look sequences may be obtained by rotating the head of the test person while the test person fixes on a single control point. This represents a particularly simple method of obtaining different positions of the control point on the field of view video, the definition of a single physical control point sufficing.

In a further embodiment of the present invention, between 25 and 100 positions of the control point(s) may be used. The very high precision of the correlation function desired results in this way, with reasonable computer outlay at the same time.

In a further embodiment of the present invention, a result video is generated from the field of view video and the established coordinates of the visual point on the field of view video, on which the visual point is displayed by a clearly visible mark, particularly a cross. This allows a particularly graphic representation of the results, which is therefore advantageous for more rapid analysis of the look sequences.

Furthermore, the present invention relates to a method for detecting, evaluating, and analyzing look sequences of a test person using a look detection system,
the field of view of the test person being detected by a first camera, which is directed forward and firmly held on the head of the test person, and being recorded in a field of view video,
for each frame of the field of view video, the coordinates of the corresponding visual point, i.e. the point upon which the test person fixes, being established on the field of view video.

In this method, which is known in the related art, there is often the problem of evaluating the measured values. In particular, the problem results, during recording of all frames on a video system, of further processing and analyzing these significant quantities of data in compressed form.

It is therefore a further object of the present invention to compress the very large quantities of data resulting during detection of the look sequences into a form optimum for analysis and therefore offer a possibility of analyzing the detected look sequences in a simple way. It is a further object of the present invention to preprocess the highly technical content of the field of view analysis particularly simply and represent it graphically even for lay people without professional qualifications.

This is achieved according to the present invention in that multiple categories are defined and the visual point for each frame is assigned to a category, in that, for each frame, it is checked which category the visual point lies in the region of.

From this, the possibility results of straightforwardly arranging the large quantity of data, which results through the evaluation of the look sequences, according to categories. Since the pupil coordinates of each frame no longer have to be processed further, but rather only the coordinates of the different defined categories, a drastic reduction of the data volume results.

In a further embodiment of the present invention, for compressed representation of the time sequence of the association of the visual point to specific categories of a look sequence, a diagram is produced which has two axes, one axis corresponding to a time axis and the other axis corresponding to the individual categories, it being established for each frame in which category the visual point is located and a visual mark being entered in the diagram at the height of the time axis corresponding to the instant of the frame and the height of the other axis corresponding to the category. A diagram results from this which indicates the time sequence of the looks toward in a straightforward way and therefore allows simple and rapid further analysis.

According to another variant of the present invention, for compressed representation of the dwell time of the visual point on specific categories of a look sequence on a static image
for each category, it is established for which frames the visual point lies in a category,
the dwell time of the visual point on this category is established by addition of the duration of these frames, and
an image is produced which corresponds to the static image, in which a graphic element, which has at least one parameter which is proportional to the dwell time, is positioned in the region of each category.

In this way, a diagram results which straightforwardly indicates the total duration of the looks toward individual categories. The essential information from all frames of the field of view video and all pupil coordinates of the frames of the eye video is therefore summarized in this diagram, only one single graphic element having to be used per category.

In order to obtain a diagram which straightforwardly indicates the sequence of looks toward individual categories, according to a further embodiment of the present invention, for compressed representation of the sequence of look sequences, a perspective or undistorted representation of the scene observed by the test person is produced and an arrow is assigned to each visual point therein.

Furthermore, the present invention relates to a method for detecting, evaluating, and analyzing the looking behavior of various test persons in a predetermined examination situation.

Due to the lack of exact evaluation of the look sequences of a test person according to the present invention, studies involving quantitative comparison of the looking behavior of multiple test persons in one and the same situation have been unknown until now.

It is therefore a further object of the present invention to allow the simple and exact analysis of the looking behavior of various test persons in a predetermined and exactly reproducible examination situation.

This is achieved according to the present invention in that the examination situation is recorded and this recording is played back for each test person, their look sequences being detected and evaluated using a look detection system,
the field of view of the test person being detected by a first camera, which is directed forward and firmly held on the head of the test person, and being recorded in a field of view video,
for each frame of the field of view video, the coordinates of the corresponding visual point, i.e. the point on which the test person fixes, being established on the field of view video.

In this way, the looking behavior of various test persons may be analyzed very simply for the same examination situation. This makes it possible to evaluate, for example, looking behavior which is a function of age or the physical state of the test persons.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Throughout all the Figures, same or corresponding elements are generally indicated by same reference numerals.

A look detection system intends to illustrate as accurately as possible, which point of the field of view a test person looks at, i.e., upon which exact point the interest and/or the attention of the test person is directed.

The field of view is hereby detected with a first camera 1, which is directed forward and firmly held on the head of the test person. Furthermore, the movement of the pupil of the test person is detected by a second camera 2, which is also firmly held on the head. Both cameras 1, 2 are firmly held on the head of the test person in such a way that they follow the movement without restricting the freedom of movement of the head and eyes. From the evaluation of these two recordings it is possible to indicate with great precision which at point the test person looks at any moment. In this way, exact statements about looks toward, staring, and the absence of looks are possible.

Such look detection systems are preferably used in the safety field, particularly in the field of accident research, but also in the field of advertising or in other investigations of human physiology.

Overall, looking behavior research represents a significant building block for the research of physiological causes of accidents. For example, new information for explaining accidents and reconstructing accidents in regard to human performance limits may be found through comprehensive look investigations.

Typically, for example, particularly dangerous places in street traffic are investigated using look detection systems. A test person equipped with such a look detection system travels through the dangerous location in this case, their looking behavior being recorded. The sum of the looks analyzed in this case will subsequently be referred to as a look sequence. From the analysis of the looking behavior, it is possible to reconstruct which signposts or signals are not sufficiently observed due to their unfavorable placement, or where particularly obscured and/or little noted locations lie in an intersection.

In the field of work safety, e.g., on construction sites, it may be investigated which sources of danger are detected very late by the test person, and which safety precautions would be necessary in this case.

A further important field of application of look detection systems is the analysis of advertising posters or advertising spots. In this case as well, it is possible to detect very precisely which messages, texts, logos, etc. are fixed on by the test person, for how long, and in which sequence.

Figures 1, 2:
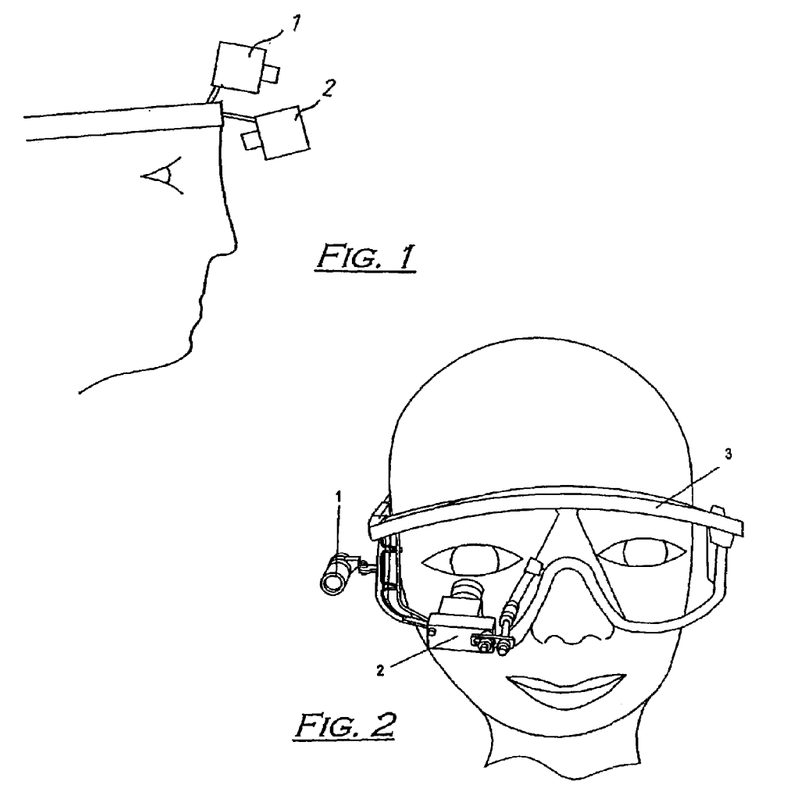
FIG. 1 is a schematic illustration of the part of the image detection system firmly held on the head of the test person.
FIG. 2 shows an illustration of the part of the image detection system firmly held on the head of the test person, which includes eye glasses.

FIG. 1 shows a part of a look detection system for performing the method according to the present invention. The field of view of the test person is detected by a first camera 1, which is directed forward and firmly held on the head of the test person. This first camera 1 therefore provides an approximate image of the look direction of the test person, which is purely defined by the position of the head. First camera 1 may, for example, be implemented by a CCD color camera, which records a large part of the field of view of the test person.

Preferably, first camera 1 and/or also second camera 2 may additionally be controlled using software and thus be adjusted to greatly differing external use conditions. This ensures that there is no distortion of the pupil image due to the direct recording of the pupil and/or a large image exists due to the direct proximity to the eye and the device may be kept smaller as a whole. Both the size and the generally poor image quality represented significant causes for imprecision in previous methods. This led not only to difficulties in the weight of the look detection system, but also to general restrictions in the looking behavior of the test person, which may be avoided through the method according to the present invention. Therefore, the look detection system according to the present invention may also be used by test persons wearing different clothes and protective measures, such as a helmet, without restrictions. Different cameras having different lenses may also therefore be used very easily, depending on the requirements of the experiment.

The high-quality cameras which are used in the system according to the present invention are preferably equipped with a control unit which allows white balancing, color balancing, and lighting to be performed automatically. These values are typically also manually adjustable. Through this control unit, it is possible to optimally tailor the image quality to the experiment conditions. Therefore, a very high image quality is ensured for further analysis. Furthermore, there is preferably the option of electronically enlarging an image detail as a digital zoom. As a rule, other adjustment possibilities only have a limited influence on the image generated.

The movement of the pupil of the test person is detected by a second camera 2, which is also firmly held on the head of the test person, and which is pointed toward one of the two eyes of the test person. Second camera 2 may, for example, be implemented by a black and white CCD camera and register the eye movements of the right eye. The detection of the pupil position by second camera 2 is performed directly in the look detection system illustrated in the figures, second camera 2 being pointed directly toward the eye of the test person. The detection of the pupil position may, however, also be performed via optical deflection systems such as mirrors or glass fiber cables, using which the image of the eye is deflected to second camera 2.

Both cameras 1, 2 are preferably attached to a helmet or eye glasses 3 (see FIG. 2), or a similar carrier device, preferably easy to put on and take off, which is firmly held on the head of the test person. Rigidly connected is to be understood to mean, as already explained above, that the carrier device and both cameras 1, 2 follow all movements of the head, the freedom of movement of the head and eyes not, however, being restricted in any way. The attachment of the camera onto glasses 3, as a carrier device which is easy to put on and take off, allows particularly great mobility of the test person and allows a much greater multiplicity of experiments than in typical systems.

Of course, it is also possible to provide multiple second cameras 2, in order to record both pupils of the test person, for example. Multiple first cameras 1 may also be provided, in order to completely detect the field of view of the test person, if the focal distance of one single first camera 1 is not sufficient for this purpose.

In this way, individual look sequences may be detected and, as described in the following, evaluated and analyzed. The term look sequence refers in this case to the sum of the respective looks recorded and analyzed.

Figure 3:
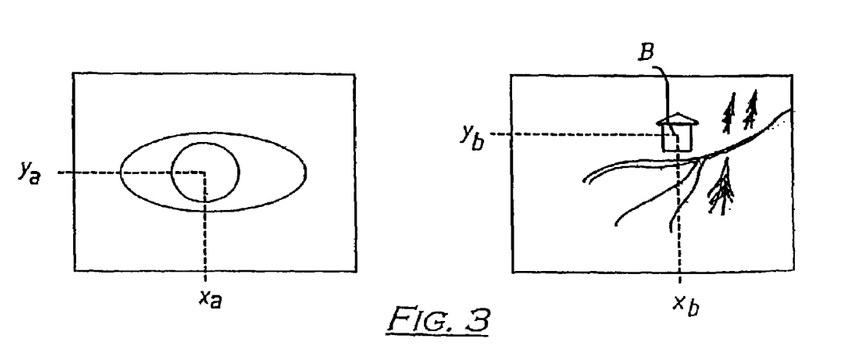
FIG. 3 shows a schematic illustration of two frames, one from the eye video and one from the field of view video.
Figure 4:
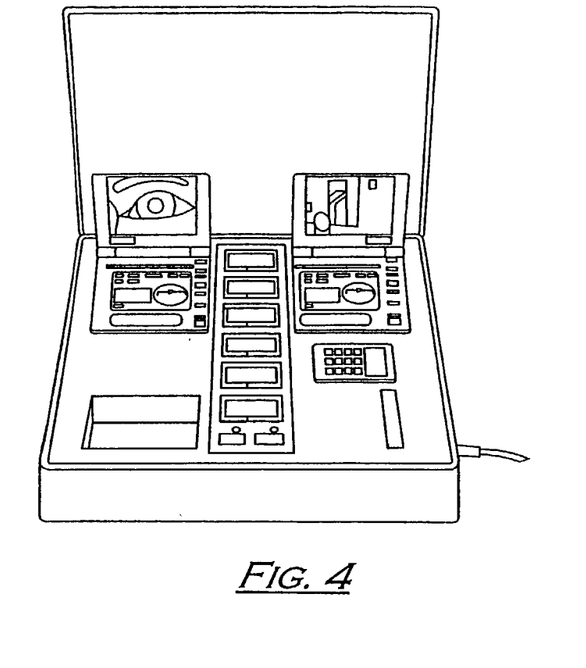
FIG. 4 shows an illustration of a video system for recording the two video signals.

With the two cameras 1, 2, one obtains two video signals, referred to in the following as eye video and field of view video and schematically illustrated in FIG. 3, which are recorded on a video system illustrated in FIG. 4.

The term video system refers in this case to all devices which are suitable for recording film data. The carrier material for recording the video signals is unimportant here. Analog film materials may be used, as well as videotapes or digital storage media such as DVDs or similar things. The storage of single images in the memory of a computer is also considered recording according to the present invention. The format is also unimportant. Different analog or digital film formats, such as DV or MPEG2, may be used. If CCD cameras are used, both sets of image information are preferably recorded on a digital video system, for example on 2 mini-DV recorders.

In a preferred embodiment, the connection between cameras 1, 2 and video system is also implemented for the first time via a radio link. This allows wireless transmission of the video signals to the video system. In this way, the unhindered movement of the test person as a pedestrian, as a bicyclist in open terrain, or even in specific work uses, such as on scaffolds or construction sites, is advantageously made possible.

It is essential that both video signals are synchronized, i.e., that for each frame of the eye video, the corresponding frame of the field of view video may be found, and vice versa. The synchronization may be performed using a periodic signal generator and a time code. Preferably, the recording method is synchronized using a pulsed tone, which is also recorded on the respective audio tracks. This method makes it possible to also simultaneously synchronize other external devices, such as accident data recorders, GPS systems, etc., in order to be able to directly synchronize additional technical and medical parameters, such as the current exact location or even heart rate, skin resistance, etc. with the looking behavior of the test person. Synchronization is necessary for subsequent processing and/or evaluation of the two video signals.

In the method according to the present invention, the precise coordinates (xa,ya) of the pupil center in the eye video are established by an image recognition program. In this case, the pupil coordinates (xa,ya) are established for each frame of the eye video. The pupil coordinates (xa,ya) in one frame of the eye video are sketched in FIG. 3.

The pupil coordinates (xa,ya) are preferably established automatically using an image recognition program. For this purpose, the contrast of the pupil to the surroundings is registered for each frame of the eye video and all points of the frame which are darker than a set degree of darkness are searched for. Using these-points, a dark area is completely detected and delimited, and subsequently the centroid of this dark area is established automatically. Since the dark area corresponds to the pupil of the test person, the centroid of the dark area represents the pupil center.

Preferably, the image recognition program offers adjustment variants for the corresponding contrast and the degree of darkness, so that the highest possible stage of precision may be achieved for all frames. Therefore, for differing illumination ratios, the respective best contrast may be ensured for each frame in the form of a grayscale threshold, which overall makes perfectly reliable determination of the pupil coordinates (xa,ya) possible.

The grayscale threshold is the value which, for example, in digitized form lies between 1 and 256 and defines the percentage proportion of black and/or white on a pixel. The highest achievable value corresponds to completely black, the lowest value to white. Since the pupil never reaches the entirely black value during recording, a value is to be defined which—at least for this image—corresponds to the actually existing pupil gray. The threshold value excludes all pixels which are lighter than the defined grayscale, all darker regions are used for finding the centroid. Three parameters allow the threshold definition to be optimized. Since the illumination ratios often change greatly during the experiments within a sequence, this threshold definition is preferably also possible individually for each frame. All adjustments corresponding to the high requirements for each frame of the sequence may therefore be stored in a file. Through the method according to the present invention, the particularly high precision in the assignment of the pupil coordinates (xa,ya) on the field of view is possible. The respective precision stage may be visualized, for example, in the form of a scale. In this case, the quality of the area established is illustrated in the evaluation program using the scale, it primarily being important that a positive value is achieved. Negative values have the consequence that the respective frame is rejected. The higher the positive value, the more exactly light regions (surroundings) may be differentiated from dark regions (pupil).

In addition, an infrared filter may be provided in front of the camera for more precise localization of the pupil center. Through this, the contrasts in the eye video are amplified. The IR filter has two important functions: firstly, the eye is illuminated using infrared light-emitting diodes (LED), which ensure good contrasts for the eye camera and for the further processing even in absolute darkness. The filter has the task of transmitting light emitted from the LED to the camera chip, all other spectral regions of the light are suppressed in accordance with the filter transmission curve. Secondly, the reflections on the pupil caused by sunlight, which have massive negative effects on finding the centroid, are primarily in the blue spectral region. In this case as well, the filter has the task of reducing the reflections on the pupil which are caused by sunlight.

Figure 5:
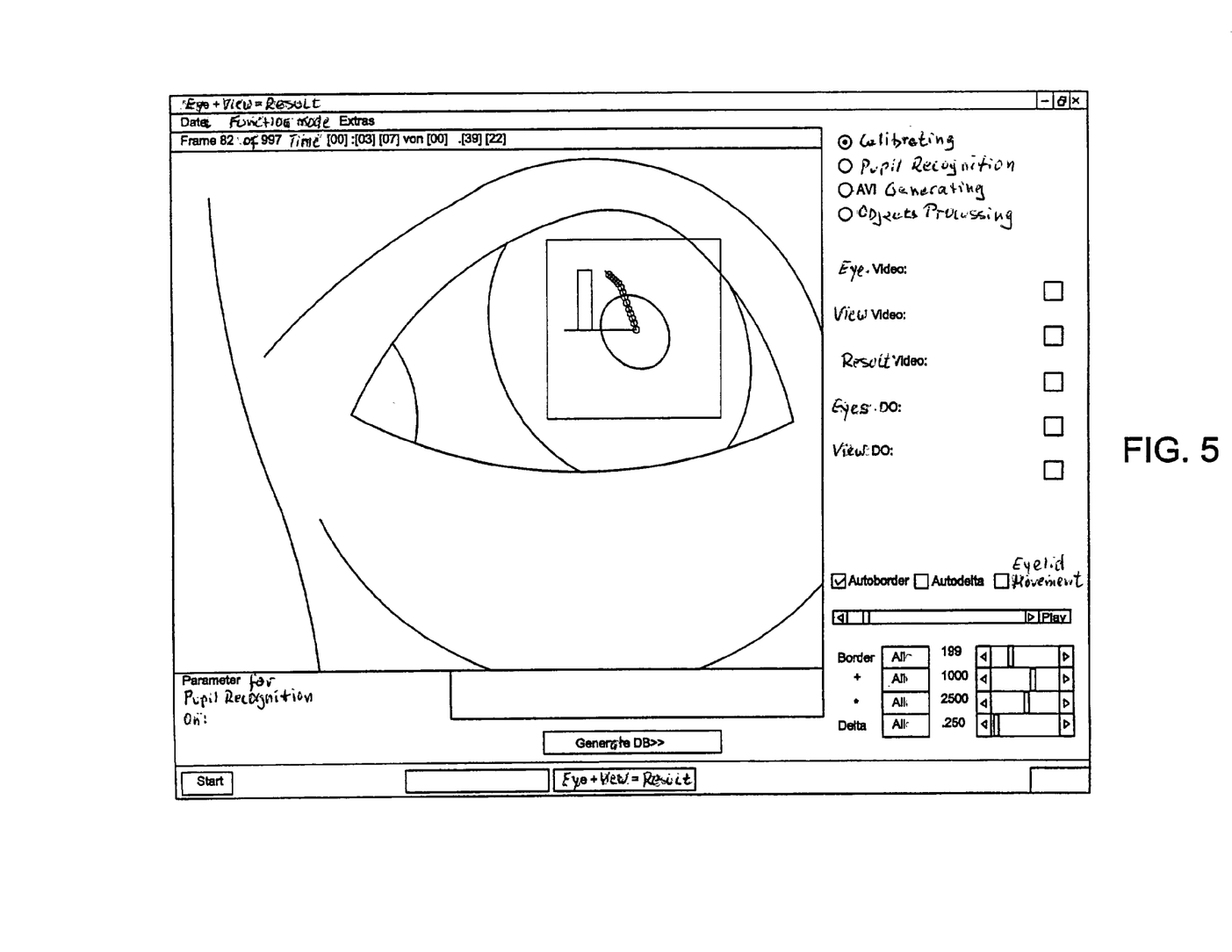
FIG. 5 shows the illustration of a user interface for establishing the pupil coordinates (xa,ya) according to the present invention.

The pupil coordinates (xa,ya) can also be checked manually after having been established automatically. A technician may manually change the image processing parameters in the event of an erroneous automatic detection (which may occur, for example, in the event of sudden reflected glare on the eye surface, etc.). It is also possible to correct the pupil coordinates (xa,ya) directly. A user interface for the computer localization of the pupil center according to the present invention and the manual check is shown in FIG. 5.

Overall, the pupil coordinates (xa,ya) are obtained for each frame of the eye video in the form of a Cartesian pair of values, for example. Of course, other coordinate systems, such as polar coordinates, etc., may also be used.

Since both cameras 1, 2 are firmly held on the head of the test person, a specific position of the pupil and/or of the pupil center in the eye video always corresponds to a precisely defined visual point B in the field of view video. Therefore, it may be calculated precisely which point the test person looks at from the eye video and the field of view video.

For the assignment of the pupil coordinates (xa,ya) to the coordinates (xb,yb) of corresponding visual point B, i.e., the point on which the test person fixes, correlation function K between these two coordinate pairs (xa,ya) and (xb,yb) on the field of view video must first be established. The correlation between pupil coordinates (xa,ya) and visual point B on the field of view video is performed via an experimental series. For this purpose, the test person fixes on predetermined control points P in sequence. The correlation function K between pupil coordinates (xa,ya) and the coordinates (xb,yb) in the field of view video is produced with reference to the data measured in this case.

The correlation function K between pupil coordinates (xa,ya) on the eye video and the coordinates (xb,yb) of corresponding visual point B on the field of view video is preferably established automatically. For this purpose, first one or more sample look sequences of the test person on one or more specific predetermined control points P are recorded. Sample look sequence is to be understood as a look sequence which is only recorded for calibration and during which the test person looks at predetermined control points P.

Figure 6:
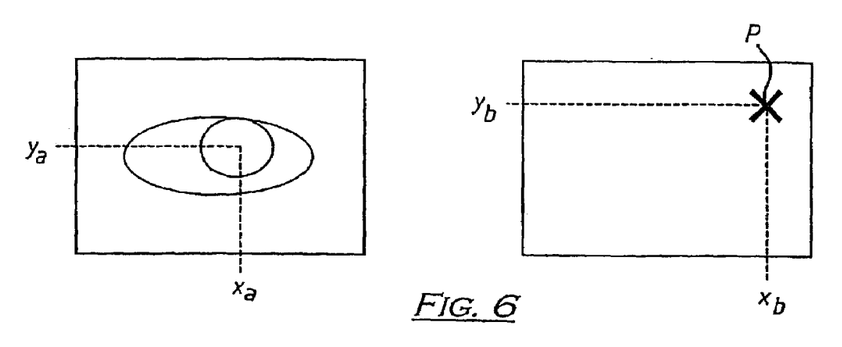
FIG. 6 shows a schematic illustration of two frames, one from the eye video and one from the field of view video, during the recording of a sample look sequence.

For example, a specific control point P may be marked on a wall. In order to obtain the best possible contrast, a black mark on an otherwise white surface may be selected as control point P, for example. Control point P is, as a rule, a cross or a point of light or something similar. The test person is instructed to fix on this control point P. the field of view and the eye of the test person being recorded by both cameras 1, 2. In this way, multiple control points P may be defined. It is also possible to mark only one control point P and instruct the test person to perform different movements with the head as he fixes on this control point P. Two frames of eyes and field of view videos obtained in this way are sketched in FIG. 6.

Since visual point B on the field of view video of the sample look sequence recorded in this way is given by known control point P. in a next step, correlation function K between the pupil coordinates (xa,ya) on the eye video and the coordinates (xb,yb) of corresponding visual point B on the field of view video may be established.

For this purpose, the pupil coordinates (xa,ya) in the eye video are established according to the method described above for each frame in the eye video.

Furthermore, the coordinates (xb,yb) of control point P in the corresponding frame on the field of view video are established. This is preferably performed using an image recognition method, which establishes the coordinates (xb, yb) of control point P, uniquely identifiable due to its contrast, on the field of view video.

However, it is also possible to determine the coordinates (xb,yb) of control point P. in the field of view video for each frame by hand, for example through a mouse click method. This allows evaluation of the sample look sequence even for difficult conditions in the field, in which automatic determination of the coordinates (xb,yb) of control point P is not possible, for example due to a background which is too non-uniform.

Therefore, the pupil coordinates (xa,ya) in the frame of the eye video may be assigned to the coordinates (xb,yb) of control point P in the corresponding frame of the field of view video.

The corresponding coordinates in the eye video and in the field of view video are established and stored for each frame of the sample look sequence.

Figure 7:
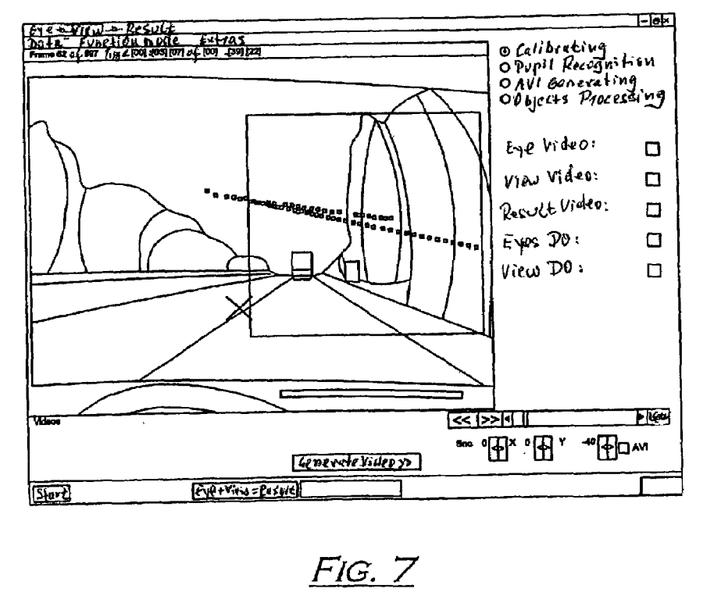
FIG. 7 shows the illustration of a user interface for establishing correlation function K according to the present invention.

The pupil coordinates (xa,ya) on the eye video and the coordinates (xb,yb) of corresponding visual point B on the field of view video are correlated from all of the data sets thus obtained, preferably through quadratic regression. Of course, other methods such as linear regression or stochastic models are also possible for the correlation. A user interface for the establishment of correlation function K according to the present invention is illustrated in FIG. 7.

A correlation function K: (xa,ya)→(xb,yb) is obtained, which uniquely assigns a specific set of the pupil coordinates (xa,ya) on the eye video to the corresponding coordinates (xb,yb) of visual point B in the field of view video.

For the greatest possible precision of correlation function K, at least 25 different positions of control point P are to be used. Above approximately 100 different control point positions, the precision achieved hardly increases any further, so that further elevation of the number of control point positions is no longer advisable. Therefore, between 25 and 100 control point positions are preferably used.

Using the correlation function K established in this way, all subsequent video sequences of the same experimental series, i.e., in which there are no changes in regard to the camera positions on the head of the test person, may be calculated.

Non-linear connections may be detected through the numeric correlation of the two coordinate pairs. This offers a significant advantage in relation to known systems, in which the two video signals are simply superimposed. The result in these known methods is a result video which shows the field of view of the test person. The pupil of the test person is superimposed over the field of view, so that it may be seen which point is fixed on by the test person. These known methods are, however, very imprecise. Geometric displacements between the position of the pupil in the eye video and the visual point must be compensated using video technology. In the method according to the present invention, these types of geometric factors do not have to be considered. The correct assignment of the pupil coordinates (xa,ya) to visual point B is performed via correlation function K.

After the calibration of the look detection system, individual look sequences may now be detected and analyzed. After correlation function K is completely established, for each frame, the coordinates (xb,yb) of corresponding visual point B on the field of view video are extrapolated from the pupil coordinates (xa,ya) on the eye video.

The combination of the eye video and the field of view video into a result video is performed using software in such a way that calculated visual points B are positioned as centers of the looks toward on the field of view video. Through the computer determination of the coordinates (xb,yb) of visual points B according to the present invention, particularly precise representation of the center of the look toward is possible.

Figure 8:
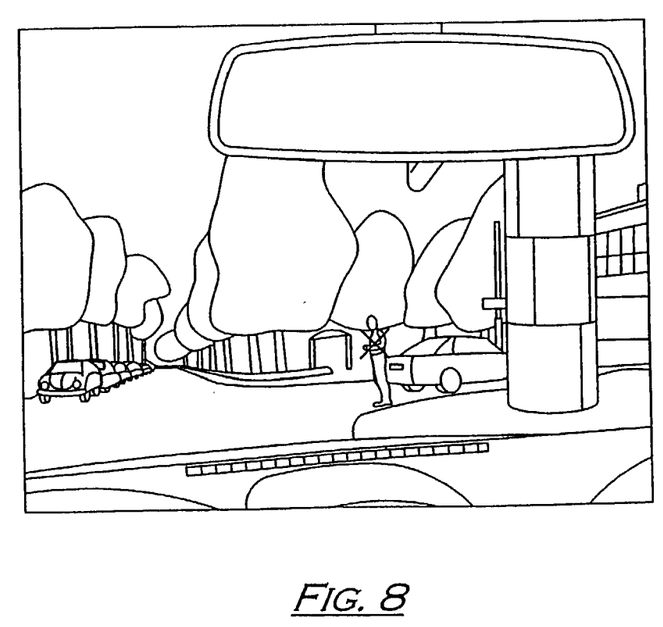
FIG. 8 shows a frame from a result video.

Visual point B may be precisely drawn on the result video. Preferably, visual point B is indicated on the result video by a clearly visible mark, for example by a cross. FIG. 8 shows a frame of a result video generated in such a way.

In a next step, the result video may be stored as a separate file and optionally compressed using conventional video compression methods.

The method according to the present invention may be performed completely automatically. In this case, checking the pupil coordinates (xa,ya) by hand is not provided. These coordinates are established directly from the frames of the eye video via the image recognition program. Furthermore, the coordinates (xb,yb) of control points P are automatically established during the calibration step. Therefore, the further storing of the entire eye video described above is no longer absolutely necessary.

The processing software can advantageously organize the field of view into different units, categories ki. The respective image contents may be assigned to freely selectable and definable categories ki.

This division into categories ki is advantageous not only for the method according to the present invention, but also for other methods for detecting, evaluating, and analyzing look sequences, in which the field of view of the test person is detected by a first camera 1 and the coordinates (xb,yb) of corresponding visual point B on the field of view video are established for each frame of the field of view video.

Figure 9:
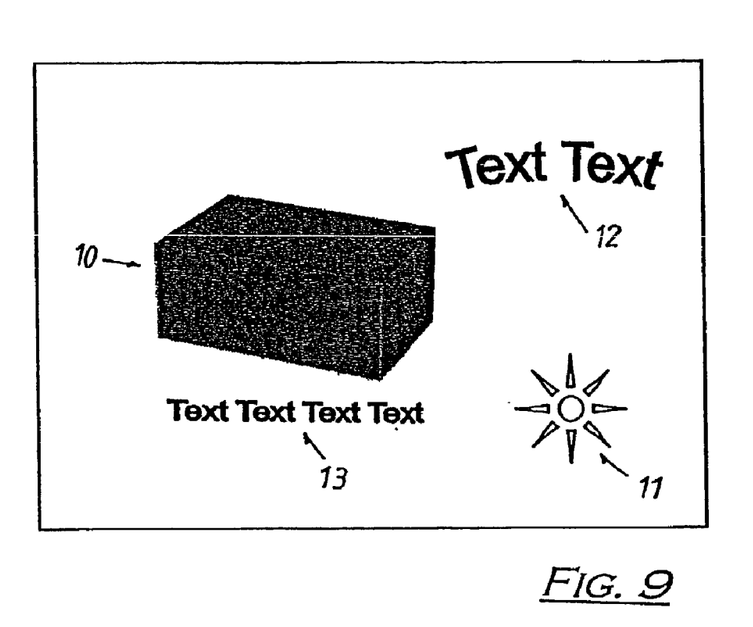
FIG. 9 shows a sketch of an image to be analyzed.
Figure 11:
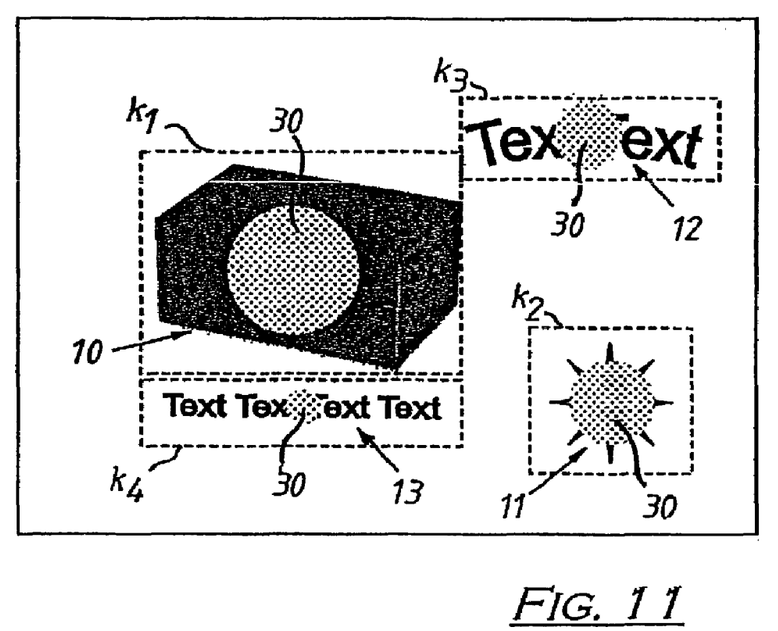
FIG. 11 shows a diagram according to the present invention for compressed representation of the dwell time of visual point B on specific categories ki of a look sequence on the static image sketched in FIG. 9.

Categories ki k1 . . . kn may be static or moving elements of the field of view. For example, in a flight simulator, one category ki may be represented by a foreign airplane, a further category by an altimeter, etc. In advertising posters, one category ki may be given by a specific logo, another by a specific text, etc. For example, the image and/or sign or advertising poster sketched in FIG. 9 contains a graphic image 10, a logo 11, a title 12, and an explanatory advertising text 13. During the analysis of the look sequences on this static image, each of these elements may be assigned its own category ki. In FIG. 11, graphic image 10 is assigned to category ki, logo 11 to category k2, title 12 to category k3, and explanatory advertising text 13 to category k4.

The assignment of the individual visual points to individual categories ki may be performed automatically. It is essential that multiple categories ki are defined and visual point B for each frame is assigned to a category ki, in that for each frame it is checked which category ki visual point B lies in the region of. If visual point B does not lie in any of defined categories ki, it may be assigned to an additional null category.

For example, in the case of a static image, individual categories ki may be defined on the basis of the frequencies of the visual points. Therefore the division into categories ki occurs completely automatically. For moving images, as in the case of the flight simulator cited, the moving objects may be recognized and localized by special image recognition software. Communication between the flight simulator and the image recognition system is also possible, in which the coordinates (xb,yb) of the individual airplanes, and/or categories ki, may be read in directly.

On the other hand, the assignment of the visual points by hand to individual categories ki for each frame is also possible.

By providing the data in digitized form, the method according to the present invention allows further preprocessing of the data, particularly the assignment of individual visual points B to different categories ki, which greatly simplifies their analysis.

Figure 10:
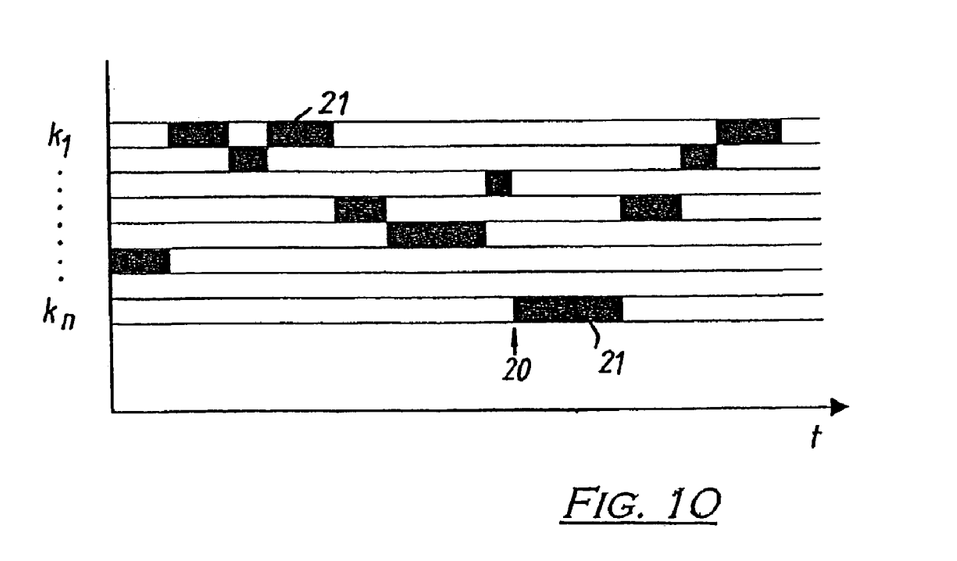
FIG. 10 shows a diagram according to the present invention for compressed representation of the time sequence of the association of visual point B to specific categories ki of a look sequence.

Advantageously, for a compressed representation of the time sequence of the association of visual point B to a specific category ki of a look sequence, a diagram can be produced which has two axes, one axis corresponding to a time axis and the other axis corresponding to individual categories ki. For this purpose, it is established for each frame which category ki visual point B is located in and a visual mark 20, for example a line, is entered in the diagram at the height of the time axis corresponding to the instant of the frame and the height of the other axis corresponding to category ki.

The linear look band generated in this way, which is shown in FIG. 10, is a form of illustration in which the time, in seconds or frames, is represented on one axis and freely selectable categories ki are listed on the other axis. By entering single visual marks 20 and/or single lines for each frame in accordance with the assignment of visual point B to one of listed categories ki, a bar illustration results, in which each bar 21 indicates the beginning and the ending of a look toward a specific category ki. The temporal sequence of maintaining the look of the test person on specific categories ki is therefore clearly visible over time as a diagram. Of course, other visual marks 20, such as dots, crosses, etc. may also be used.

Of course, it is also possible to enter additional information which goes beyond video evaluations in the linear look band. This includes information which describes the action sequence, such as changes in the street space, but also additional information from other data sources, such as accident data recorders (speed, direction), or, furthermore, other data of human physiology such as the pulse rate or blink rate, the body temperature, etc.

In the linear look band, in accordance with the respective time sections, categories ki may be centrally illustrated by bars 21, which symbolize categories ki in various colors. Summaries may then be made within these single categories ki, which then may be differentiated by color according to their content, such as location differences or differences in content such as left/right or front/back. The linear look band is, in principle, not limited in its length or in its categories ki. In order to allow a straightforward form of illustration, it is, however, advisable to summarize the contents of sections.

In a further advantageous form of illustration of the procedures during a look sequence on a static image, i.e., on a non-moving image, such as an advertising poster, the dwell times of visual point B on different categories ki may be graphically illustrated. For this purpose, it is established, for each category ki, during which frames visual point B lies in the region of this category ki. The times for which visual point B lies in the region of this category ki are added up, the sum established in this way corresponding to the dwell time of visual point B on this category ki. Subsequently, a graphic and/or an image is produced from the different dwell times, which essentially corresponds to the static image, however, each dwell time on individual categories ki being illustrated by a graphic element 30, which is placed in the region of category ki and has at least one parameter—diameter, color, etc.—which is proportional to the dwell time. For example, different dwell times may be illustrated by graphic elements 30 having different sizes (for example the circumference of graphic element 30 is larger the longer the dwell time is) or different colors. FIG. 11 shows the diagram obtained from the advertising poster of FIG. 9, in which the dwell times on individual categories ki are indicated by graphic elements 30, which are implemented as clouds of points having different diameters. Furthermore, the delimitations of four defined categories k1 to k4 are indicated by dashed lines.

This diagram according to the present invention for compressed representation of the dwell time of visual point B on a specific category ki of a look sequence on a static image is therefore distinguished in that a graphic element, which is proportional to the dwell time, is positioned in the region of each category ki. The frequency of maintaining visual point B on a specific category ki is indicated in the diagram according to the present invention by a graphic element 30 proportional to the dwell time, such as a differently sized point.

Through this diagram, the frequencies and the time overhead analysis may be visualized particular clearly. The diagram according to the present invention allows high-quality and straightforward analysis of the frequencies the looks toward.

In a further form of illustration, the field of view sketch, the look sequences are listed in the sequence in which they appear in the result video. In this case, perspective illustrations or undistorted illustrations of the scenes observed by the test person may be used, such as profile or outline sketches. For profile sketches, the look sequences may be drawn up graphically in a screen shot in photos drawn up in parallel, or also in sketches. For outline sketches, layout plans, stylized plans, or overview illustrations may be used for concrete contents. In the field of view sketch, each visual point, and/or each fixation, is assigned an arrow, independent of the fixation length. The fixation lengths and/or thematic connections may be described in more detail by colors, or also through additional information. Numberings and/or explanatory text are possible as additional information. Temporal connections and different color scales may also be displayed as a supplement, i.e., times may be bundled and identified in a concrete color having corresponding legends.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A method for detecting, evaluating, and analyzing look sequences of a test person in an environment using a look detection system comprising the steps of:
   detecting a field of view of the test person with a first test camera, said camera pointing forward and being firmly held on the head of the test person so as to provide the test person an unimpeded view of the environment, said field of view being recorded in frames of a field of view video,
   detecting a pupil image of at least one of the pupils in the eyes of the test person with a second camera, said second camera being also firmly held on the head of the test person, said pupil image being recorded in frames of an eye video;
   recording each frame of the eye video at the same time as a corresponding frame of the field of view video is recorded;
   automatically determining pupil coordinates for a center of said pupil image in each frame of the eye video;
   instructing the test person to look at a respective given object in the environment at at least one respective given time, a respective given frame of the eye video corresponding to each respective given time when the test person looks at said respective given object, said respective given object being located at a respective given visual point in the field of view shown in each corresponding frame of the field of view video;
   determining location coordinates for said respective given visual point in each corresponding frame of the field of view video;
   establishing a correlation function between the pupil coordinates in given frames of the eye video and the location coordinates of said respective given visual point in the field of view shown in each corresponding frame of the field of view video; and
   extrapolating from pupil coordinates determined from a selected frame of the eye video the location coordinates of the respective selected visual point in the corresponding frame of the field of view video using said correlation function, the location coordinates of said respective selected visual point indicating where in the environment the test person was looking at a time other than a given time.

2. The method of claim 1, wherein the pupil coordinates are manually corrected after the pupil coordinates have been determined automatically.

3. A method for detecting, evaluating, and analyzing look sequences of a test person in an environment using a look detection system, comprising the steps of:
   detecting a field of view of the test person with a first test camera, said first camera pointing forward and being firmly held on the head of the test person, said field of view being recorded in frames of a field of view video;
   detecting a pupil image of at least one of the pupils in the eyes of the test person with a second camera, said second camera being also firmly held on the head of the test person, said pupil image being recorded in frames of an eye video; recording each frame of the eye video at the same time as a corresponding frame of the field of view video;
   automatically determining pupil coordinates for a centroid of said pupil image in each frame of the eye video;
   instructing the test person to look at a respective given object in the environment at at least one respective given time, a respective given frame of the eye video corresponding to each respective given time when the test person looks at said respective given object, said respective given object being located at a respective given visual point in the field of view shown in each corresponding frame of the field of view video;
   recording at least one look sequence, said look sequence providing a plurality of respective given frames of an eye video and corresponding frames of a field of view video;
   determining location coordinates for said respective given visual point in each corresponding frame of the field of view video;
   associating the pupil coordinates in each given frame of the eye video with location coordinates of the respective visual point where the respective given object is located in the corresponding frame of the field of view video in a look sequence;
   storing the associated pupil coordinates and location coordinates as a data set;
   establishing a correlation function between said pupil coordinates in said given frames of the eye video and said location coordinates of the respective visual point in said corresponding frames from said data set; and
   extrapolating from pupil coordinates determined from a selected frame of the eye video the location coordinates of the respective selected visual point in the corresponding frame of the field of view video using said correlation function, the location coordinates of said respective selected visual point indicating where in the environment the test person was looking at a time in the look sequence other than a given time.

4. The method of claim 1, wherein location coordinates for the visual where the respective given object is located in a corresponding frame of the field of view video are automatically determined using an image recognition method.

5. The method of claim 1, wherein location coordinates of the visual point where the respective given object is located in a corresponding frame of the field of view video are determined by a mouse click.

6. The method of claim 1, wherein the at least one look sequence is obtained by rotating the head of the test person to multiple head positions while the test person looks at a respective given object.

7. The method of claim 1, wherein the at least one look sequence includes between 25 and 100 given object positions.

8. The method of claim 1, further comprising the step of generating a result video from the field of view video and the location coordinates of the visual point in corresponding frames of the field of view video, said location coordinates having been extrapolated using the established correlation function, said result video indicating the visual point by a clearly visible marking.

9. The method of claim 1, further comprising the steps of
providing respective definitions for a plurality of categories for objects shown in the field of view video, and
determining which category definition is applicable to an object located at the respective visual point in a corresponding frame of the field of view video.

10. The method of claim 9, further comprising the steps of:
defining a diagram having a time axis and a category axis; and providing in the diagram a mark for the respective visual point in each corresponding frame at a respective location on the diagram corresponding to the recording time of the corresponding frame on the time axis and the category applicable to an object shown at the respective visual point in said corresponding frame of the field of view video on the category axis, thereby producing a compressed sequential representation of the look sequence.

11. The method of claim 9, further comprising the steps of:
identifying in which respective corresponding frames a given category definition is applicable to the respective visual point, determining a dwell time of the visual point in said given category by adding the duration time of each of said identified respective corresponding frames;
providing a field of view image corresponding to at least a portion of a field of view shown in said respective corresponding frames; and
providing a respective graphic element in said field of view image where an object in each respective category is located, said graphic element having at least one parameter that is proportional to the dwell time so that a compressed representation of a dwell time of the visual point in a specific category is produced.

12. The method of claim 9, further comprising the steps of
providing a field of view image corresponding to at least a portion of a field of view shown in said respective corresponding frames of a look sequence; and
indicating the sequence of visual points recorded in the look sequence with respective arrows, so that a compressed representation of the look sequence is produced.

13. The method of claim 1 further comprising the steps of:
recording a view of an environment; and displaying said recorded view of said environment back to the test person so that said recorded view provides a portion of the environment of the test person.

14. The method of claim 3, wherein the pupil coordinates and the coordinates of the corresponding visual point are correlated from said data sets through quadratic regression.

15. The method of claim 1, wherein the at least one given object is a control point mark, said method further comprising the step of placing a control point mark in the environment.

16. The method of claim 3, further comprising the step of detecting non-linearity in said data sets.

17. The method of claim 6, wherein said at least one look sequence includes between 25 and 100 head positions.

18. The method of claim 9 further comprising the step of assigning a visual point on a frame of the field of view video to a null category.

* * * * *

UNITED STATES PATENT AND TRADEMARK OFFICE
CERTIFICATE OF CORRECTION

| | | |
|---|---|---|
| PATENT NO. | : 6,997,556 B2 | Page 1 of 1 |
| APPLICATION NO. | : 10/262608 | |
| DATED | : February 14, 2006 | |
| INVENTOR(S) | : Ernst Pfleger | |

It is certified that error appears in the above-identified patent and that said Letters Patent is hereby corrected as shown below:

<u>Column 15, line 6</u>: Add after "visual" --point--

Signed and Sealed this

Twenty-first Day of November, 2006

JON W. DUDAS
*Director of the United States Patent and Trademark Office*